United States Patent
Ogawa et al.

Patent Number: 6,080,430
Date of Patent: Jun. 27, 2000

[54] POWDER COATED WITH SPARINGLY SOLUBLE ULTRAVIOLET ABSORBER

[75] Inventors: Katsuki Ogawa; Sadaki Takata; Tomiyuki Nanba, all of Yokohama; Koji Yoshino, Tokyo, all of Japan

[73] Assignee: Shiseido Company, Ltd., Tokyo, Japan

[21] Appl. No.: 09/068,110

[22] PCT Filed: Sep. 8, 1997

[86] PCT No.: PCT/JP97/03149

§ 371 Date: Jun. 22, 1998

§ 102(e) Date: Jun. 22, 1998

[87] PCT Pub. No.: WO98/09610

PCT Pub. Date: Mar. 12, 1998

[30] Foreign Application Priority Data

Sep. 6, 1997 [JP] Japan ................................. 8-257809

[51] Int. Cl.[7] ................. A61K 9/16; A61K 9/50
[52] U.S. Cl. .................... 424/490; 424/489; 424/59; 424/470; 424/459
[58] Field of Search ........................ 424/490, 489, 424/59, 63, 62, 60

[56] References Cited

U.S. PATENT DOCUMENTS

| | | | |
|---|---|---|---|
| 4,801,445 | 1/1989 | Fukui et al. | 424/69 |
| 5,000,945 | 3/1991 | Kobayashi et al. | 424/59 |
| 5,747,049 | 5/1998 | Tominaga | 424/401 |

Primary Examiner—Thurman K. Page
Assistant Examiner—William E. Benston, Jr.
Attorney, Agent, or Firm—Townsend & Banta

[57] ABSTRACT

Powder coated with a sparingly soluble ultraviolet light absorber which is prepared by a method in which the melted sparingly soluble ultraviolet light absorber and an inorganic or organic powder are mixed while heating and then gradually cooled to coat the surface of said powder with the sparingly soluble ultraviolet light absorber, or by a method in which the sparingly soluble ultraviolet light absorber is adsorbed to or made to coat the surface of the inorganic powder or organic powder using a mechanochemical method. The sparingly soluble ultraviolet light absorber can be blended in a high concentration in the system and blended homogeneously in the base agent. Also, stability over time is superior and the ultraviolet light protection effect is high.

6 Claims, 4 Drawing Sheets

POWDER COATED WITH SPARINGLY SOLUBLE ULTRAVIOLET ABSORBER

FIELD OF THE INVENTION

The present invention relates in general to powder coated with a sparingly soluble ultraviolet light absorber and particularly to powder coated with a sparingly soluble ultraviolet light absorber which can contain a high concentration of a sparingly soluble ultraviolet light absorber distributed homogeneously in the base agent, has superior stability over time and a high ultraviolet light protection effect.

BACKGROUND OF THE INVENTION

Sun tanning of the skin to a brown or light brown color is primarily done by the younger generations as an expression of healthy beauty or fashion and there are many people who want to be actively sun tanned. They apply a cosmetic on the whole body and expose the skin to intense sunlight. However, recently awareness of the importance of protecting the skin from ultraviolet light has risen and cosmetics have begun to contain an ultraviolet light absorber which absorbs ultraviolet light (wavelength 290–320 nm) known to cause blisters and erythema.

However, some ultraviolet light absorbers cannot exhibit their efficacy sufficiently although they have a high ultraviolet light absorption effect because the base agent can contain only a very small amount of them due to their very low solubility in solvents. Among them, Pongamia extract contains Pongamol which has a very strong ultraviolet light absorption effect and is expected to be useful as a ultraviolet light absorber (Japanese examined patent publication Tokko Hei 6-60092). However, its solubility is poor in all the base agents which are usually used as a base agent for cosmetics and therefore its application as it is in cosmetics and such has been very difficult.

DISCLOSURE OF THE INVENTION

Based on the aforementioned problem, the inventors conducted earnest research and discovered that a coating of a sparingly soluble ultraviolet light absorber can be formed on the surface of various kinds of powder by mixing the sparingly soluble ultraviolet light absorber with the powder in a specific manner and that, unlike the sparingly soluble ultraviolet light absorber itself, said powder can be added to a cosmetic base agent in a large amount and the stability over time is superior to when a non-sparingly soluble ultraviolet light absorber is added.

That is, the present invention provedes a powder coated with a sparingly soluble ultraviolet light absorber which comprises an inorganic or organic powder whose surface is coated with the sparingly soluble ultraviolet light absorber.

A preferable method of manufacturing it is to mix the melted sparingly soluble ultraviolet light absorber and inorganic powder or organic powder while heating and then gradually cool them to coat the surface of said powder with the sparingly soluble ultraviolet light absorber.

THE BEST MODES OF THE EMBODIMENTS

The configuration of the present invention is described below in detail.

A sparingly soluble ultraviolet light absorber used in the present invention refers to an ultraviolet light absorber whose solubility in isopropyl myristate at room temperature is 2% or less. The representative example of such a sparingly soluble ultraviolet light absorber is the pongamia extract. Additional examples include 4-(3,4-dimethoxyphenylmethylene)-2,5-dioxoimidazolidine-1-propionic acid 2-ethylhexyl ester (Softshade DH), dibenzoyl methane derivatives and Chalcone derivatives.

The Pongamia extract is a solvent extract of the seeds of Karanja and its main constituent is Pongamol. Its solubility in isopropyl myristate at room temperature is approximately 1%.

Examples of the powder used in the present invention include inorganic powders such as zinc oxide, titanium oxide, kaolin, bentonite, talc, sericite and mica titanium, inorganic spherical powders such as spherical calcium silicate (see Japanese unexamined patent publication Tokkai Sho 54-163830), spherical silica gel (see Tokkai Sho 54-140736), spherical silica gel treated with aluminum stearate and titanium-coated polyethylene beads, organic spherical powders such as nylon powder, methacrylic ester resin powder (see Tokkai Sho 59-193901), crystalline cellulose, spherical polymethyl methacrylate powder, polyethylene beads, vinyl acetate, N-vinyl pyrolidone, 2,4-diamino-6-phenyl 1,3,5-triazine, acrylic ester, styr-divinylbenzene copolymer, ethylene-vinyl acetate copolymer, vinyl chloride-vinyl acetate copolymer and ethylene tetrafluoride. Of these, the most preferable powders include kaolin, talc, sericite, mica titanium and titanium oxide.

The blend ratio between the powder and the sparingly soluble ultraviolet light absorber (powder/sparingly soluble ultraviolet light absorber) is 63/35-97/3 and preferably 85/15-92/8. If the amount of the ultraviolet light absorber is too small, then the amount of the coating is small and a sufficient ultraviolet light protection effect cannot be obtained when the mixture is blended into a cosmetic. This is not preferable because then another ultraviolet light absorber has to be added during the manufacturing process. On the other hand, if the amount of the ultraviolet light absorber is too large, then the amount of the coating is large and the powder tends to be an unmixed-in lump of flour. This is not preferable because then dispersivility (dispersion) in the cosmetic becomes poor and homogeneous distribution of the powder in the whole cosmetic will not be achieved, resulting in an insufficient ultraviolet light protection effect.

The powder coated with the sparingly soluble ultraviolet light absorber of the present invention can be obtained by mixing the melted sparingly soluble ultraviolet light absorber and an inorganic powder or organic powder while heating and gradually cooling them to coat the surface of said powder with the sparingly soluble ultraviolet light absorber. This method can be implemented by the mechanofusion treatment, the thermal Henshell mixer treatment, the hybridizer system treatment, etc.

The powder coated with the sparingly soluble ultraviolet light absorber of the present invention can also be obtained by crushing a sparingly soluble ultraviolet light absorber and physically coating an inorganic powder or organic powder with it by means of a mechanochemical method.

The powder coated with the sparingly soluble ultraviolet light absorber of the present invention can also be obtained by mixing a sparingly soluble ultraviolet light absorber dissolved in a solvent and an inorganic powder or organic powder while heating and gradually cooling the mixture to coat the surface of said powder with the sparingly soluble ultraviolet light absorber. However, the ultraviolet light protection effect of the obtained powder is inferior to those obtained by the former methods. This method can be implemented by a wet treatment using an organic solvent such as acetone or ethyl acetate.

The content of the powder coated with the sparingly soluble ultraviolet light absorber in a cosmetic is preferably 2–60 wt %, more preferably 10–40 wt %, of the total cosmetic. It is not preferable if the content of the coated powder of the present invention is less than 2 wt % because then the ultraviolet light protection effect drastically decreases. On the other hand, it is not preferable if the content of the coated powder of the present invention is more than 60 wt % because then the ultraviolet light protection effect will not increase in proportion to the increase in the content, the effect of the cosmetic base agent itself manifests prominently, spreadability becomes poor and the film becomes thick and finally the usability becomes poor because of stickiness.

In addition to the aforementioned essential ingredients, depending on the purpose, other ingredients which are usually blended into cosmetics can be blended into the cosmetic of the present invention as necessary within the quantitative and qualitative range which does not affect the effect of the present invention. Examples of these ingredients include fats oils such as olive oil, coconut oil, safflower oil, castor oil and cottonseed oil, waxes such as lanolin, jojoba oil and carnauba wax, hydrocarbon oils such as liquid paraffin, squalane and vaseline, fatty acids, alcohols, ester oils such as cetyl octanoate and isopropyl myristate, silicone oils such as dimethyl polysiloxane and methylphenyl polysiloxane, silicone resins, humectants such as propylene glycol, dipropylene glycol, 1,3-butylene glycol, glycerine, isoprene glycol, polyethylene glycol, hyaluronic acid, chondroitin sulfuric acid and pyrolidone carboxylic acid, antioxidants such as tocopherol, butylhydroxy anisole and dibutylhydroxytoluene, preservatives such as methyl paraben, ethyl paraben, propyl paraben and butyl paraben, powders such as mica, bentonite, kaolin, talc, mica titanium, oxybismuth chloride and silicic anhydride, pearl agents such as guanine, laminate resin pearl agents and mica-titanium type pearl agents, inorganic pigments such as ultramarine blue, chrome oxide and cobalt blue, dyes such as Sudan III, Quinizarin Green SS and Quinoline Yellow, surfactants such as Span type, Tween type, POE alkyl ether type, POE-POP type, glycerine fatty acid ester type and POE glycerine fatty ester type, thickeners such as carboxyvinyl polymer, drugs such as anti-inflammatories, vitamins and hormones and perfumes.

EXAMPLES

Examples of the present invention are explained below. The present invention is not limited to these examples. The units of the blended amounts are weight percent.

1. Preparation of a powder coated with a sparingly soluble ultraviolet light absorber

Preparation Example 1

| (Recipe) | |
| --- | --- |
| Pongamia extract | 10.0 wt % |
| Sericite (Seripearl) | 90.0 |

(Preparation method)

Dry method: Powder with the composition described above was mixed using a Henshell mixer. The surface of sericite, which was the core powder, was coated with the Pongamia extract by using the mechanofusion system (from Hosokawa Micron Co., Ltd.). A 10 minute treatment at a speed of 1,500 rpm was followed by a 5 minute treatment at a speed of 2,000 rpm. The treated powder was then crushed.

Figure 2:
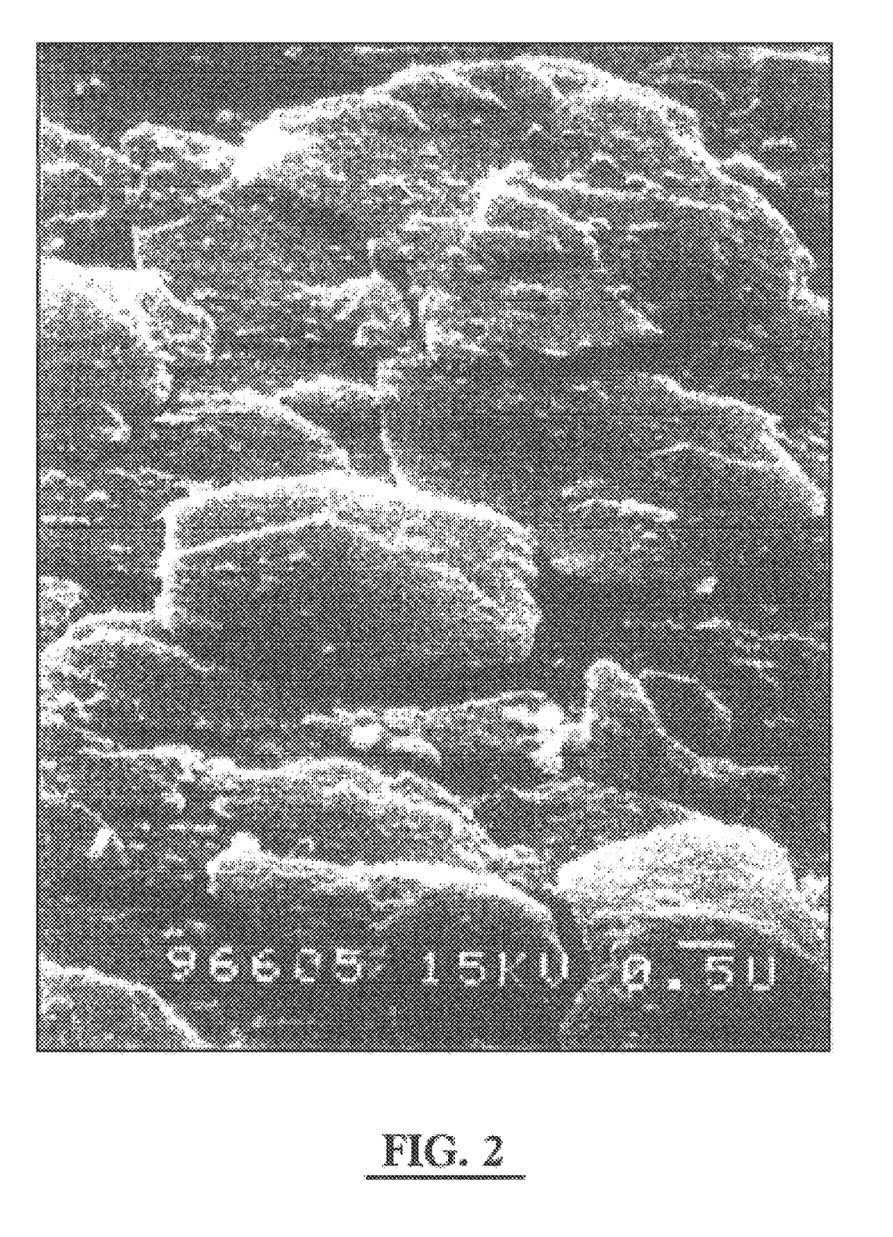
FIG. 2 is a scanned image showing the powder structure of the pongamia-extract-coated sericite powder treated with the pongamia extract.
Figure 3:
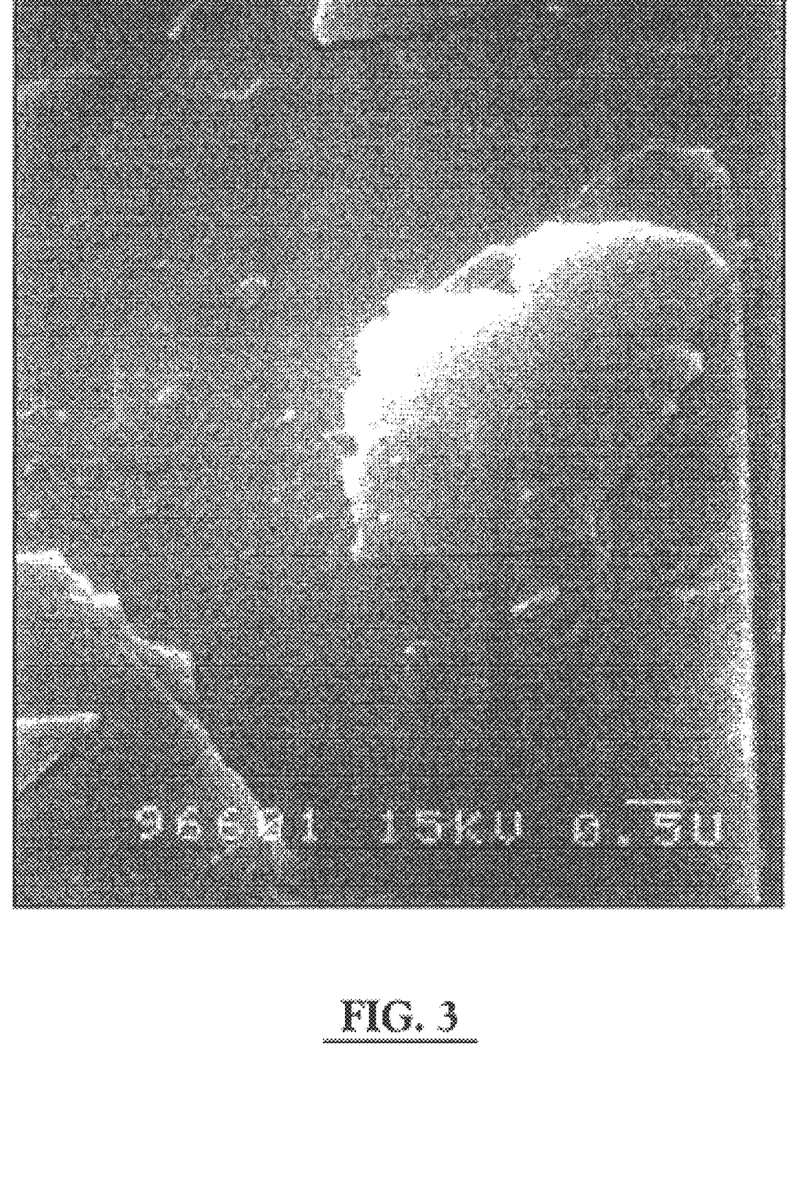
FIG. 3 is a scanned image showing the powder structure of sericite powder.

FIG. 2 is a scanned image (magnification: 10,000 times) showing the powder structure of the powder coated with the pongamia extract obtained by this preparation example. FIG. 3 is a scanned image (magnification: 10,000 times) of the raw material sericite powder. FIG. 2 indicates that the surface of the sericite is coated with Pongamia and, as a result, the powder particles are thicker and have an uneven surface compared with FIG. 3.

Preparation Example 2

| (Recipe) | |
| --- | --- |
| Pongamia extract | 10.0 wt % |
| Sericite (Seripearl) | 90.0 |

(Preparation method)

Wet method: Powder with the composition described above was made into a slurry by using an acetone solvent and the surface of sericite, which was the core powder, was coated with the Pongamia extract by using the kneader system (from Kuramochi Co., Ltd.). In the kneader system, the temperature was raised to 60° C., the sericite slurry with the pongamia extract dissolved in the acetone solvent was stirred and mixed for 30 minutes, and then acetone was suctioned away while the pressure was reduced. The powder was taken out, completely dried and crushed.

Preparation Example 3

| (Recipe) | |
| --- | --- |
| Softshage DH | 10.0 wt % |
| Sericite (Seripearl) | 90.0 |

(Preparation method)

Preparation was carried out in the same manner as in Preparation example 1.

Comparative Preparation Example 1

| (Recipe) | |
| --- | --- |
| 4-t-butyl-4'-methoxy-dibenzoylmethane (Parsol 1789) | 10.0 wt % |
| Sericite (Seripearl) | 90.0 |

(Preparation method)

Preparation was carried out in the same manner as in Preparation example 1.

Figure 1:
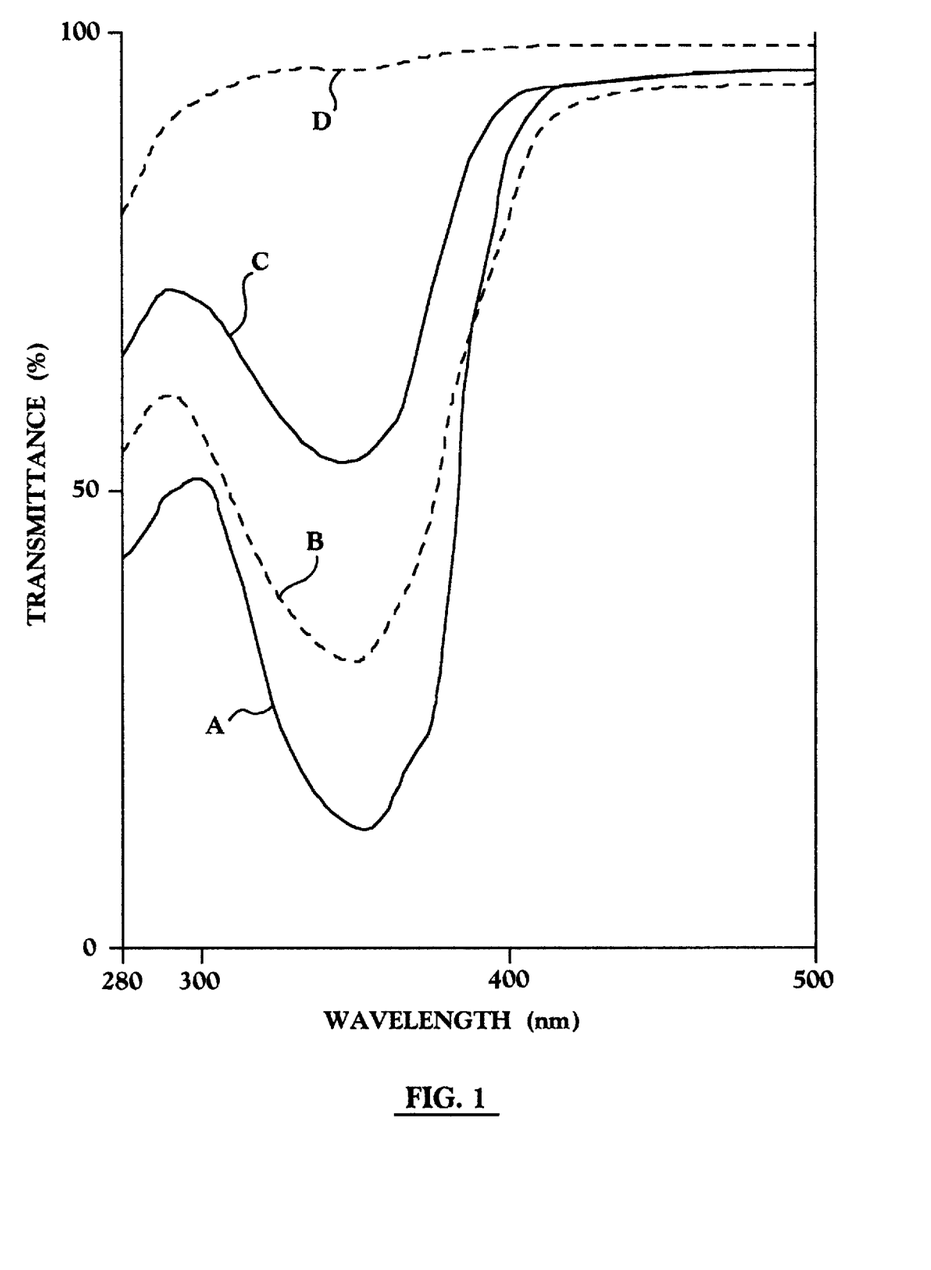
FIG. 1 shows the ultraviolet light transmittance of the powder coated with the sparingly soluble ultraviolet light absorber of the present invention in comparison with a simple blend.

2. Methods of testing the powder treated with the sparingly soluble ultraviolet light absorber Ten wt % of the powders treated with the sparingly soluble ultraviolet light absorbers obtained in Preparation example 1 and Preparation example 2 were dispersed in vaseline and, after a roller treatment, the transmittance was measured using an application amount of 2.0 mg/cm$^2$. The ultraviolet light transmittance was also measured in the same manner as above for a simple mixture of the pongamia extract and the powder (weight ratio: 1:9). The results are shown in FIG. 1. In this figure, A is Preparation example 1, B is Preparation example 2, C is the simple mixture and D is a control (sericite only).

This figure indicates that the powder treated with Preparation example 1 is the most superior in the ultraviolet light protection effect.

The treated powders obtained in Preparation example 1, Preparation example 3 and Comparative preparation example 1 were molded into solid foundations according to the recipes below and their ultraviolet light protection effect was measured. The results are shown in Table 1. In this table, Control 1 does not contain the treated powder. The measurement of the ultraviolet light protection effect was evaluated by a method (in vitro) which has a high correlation with the PFA value (in vivo) which is obtained by the PFA (Protection Factor of UVA) measurement which is a protection indicator of skin darkening caused by UVA as specified in the ultraviolet light special committee of the Japan Cosmetic Industry Association.

(Recipe)

| | |
|---|---|
| Treated powder | 20.0 wt % |
| Sericite | 20.0 |
| Calcinated mica | 20.0 |
| Synthetic mica | 7.0 |
| Titanium oxide for pigments | 4.0 |
| Barium sulfate | 2.0 |
| Iron oxide | 2.0 |
| Fine particle titanium oxide | 3.0 |
| Spherical resin powder | 8.0 |
| Ethyl paraben | Appropriate amount |
| Squalane | 4.0 |
| Glyceryl trioctanoate | 4.0 |
| Dimethylphenyl polysiloxane | 3.0 |
| Octylmethoxy cinnamate | 2.0 |
| Anti-oxidant | Appropriate amount |
| Perfume | Appropriate amount |

TABLE 1

| Treated powder | PFA value |
|---|---|
| Preparation example 1 | 6.1 |
| Preparation example 3 | 5.5 |
| Comparative preparation example 1 | 9.7 |
| Control | 5.1 |

Table 1 indicates that the PFA value of the solid foundation which uses the treated powder of Preparation example 1 is an improvement over that of the control by approximately one.

Also, the solid foundations described above were tested for stability over time by being allowed to stand for one month under the conditions indicated in Table 2. The results are also shown in Table 2.

(Evaluation method)

○: Good
Δ: Somewhat poor
×: Poor

TABLE 2

| Temperature | 50° C. | 37° C. | 25° C. | 0° C. | 40° C. Humidified |
|---|---|---|---|---|---|
| Preparation example 1 | ○ | ○ | ○ | ○ | ○ |
| Preparation example 3 | ○ | ○ | ○ | ○ | ○ |
| Comparative preparation example 1 | × | Δ | × | Δ | × |
| Control | ○ | ○ | ○ | ○ | ○ |

In terms of stability over time, the treated powder of Comparative preparation example 1 reacted with iron oxide in the foundation and turned into a chelate compound, producing a red color. On the other hand, the treated powders of Preparation example 1 and Preparation example 2 did not have problems in particular. This difference is believed to be due to the sparingly soluble characteristics and the structure of the compound.

3. Recipe examples of a cosmetic which uses the powder treated with the sparingly soluble ultraviolet light absorber Example 1

Solid powder foundation

| | | |
|---|---|---|
| (1) | Mice treated with silicone | 20.0 wt % |
| (2) | Sericite | 21.2 |
| (3) | Titanium oxide for pigments | 11.0 |
| (4) | Fine particle titanium oxide | 3.0 |
| (5) | Iron oxide | 4.0 |
| (6) | Sericite coated with pongamia extract | 20.0 |
| (7) | Spherical resin powder | 5.0 |
| (8) | Ethyl paraben | 0.3 |
| (9) | Lanolin | 4.0 |
| (10) | Squalane | 4.0 |
| (11) | Liquid paraffin | 3.0 |
| (12) | Dimethylpolysiloxane | 1.0 |
| (13) | Sorbitan sesqui isostearate | 0.5 |
| (14) | Octylmethoxy cinnamate | 3.0 |
| (15) | Antioxidant | Appropriate amount |

(Preparation method)

After homogeneously mixing the powder portion (1)–(8) with a Henshell mixer, the oil portion (9)–(15) was dripped into it and mixed with the Henshell mixer. The mixture was then crushed with a pulverizer, placed on an inner dish and pressure-molded to obtain a solid foundation.

The obtained solid powder foundation exhibited an in vivo PFA (n=10) of 8.75±1.72 and an in vitro PFA (n=8) of 8.5.

The in vivo PFA (n=10) stands for the PFA value measured using ten subjects with the method according to "Specifications for UVA prevention effect measurements by the Japan Cosmetic Industry Association" (effective on Jan. 1, 1996) stipulated by the technical committee of the Japan Cosmetic Industry Association.

Comparative Example 1
Solid powder foundation

| | | |
|---|---|---|
| (1) | Mice treated with silicone | 20.0 wt % |
| (2) | Sericite | 41.2 |
| (3) | Titanium oxide for pigments | 11.0 |
| (4) | Fine particle titanium oxide | 3.0 |
| (5) | Iron oxide | 4.0 |
| (6) | Sericite coated with pongamia extract | — |
| (7) | Spherical resin powder | 5.0 |
| (8) | Ethyl paraben | 0.3 |
| (9) | Lanolin | 4.0 |
| (10) | Squalane | 4.0 |
| (11) | Liquid paraffin | 3.0 |
| (12) | Dimethylpolysiloxane | 1.0 |
| (13) | Sorbitan sesqui isostearate | 0.5 |
| (14) | Octylmethoxy cinnamate | 3.0 |
| (15) | Antioxidant | Appropriate amount |

(Preparation method)

Preparation was carried out in the same manner as in Example 1.

The obtained solid powder foundation exhibited an in vivo PFA (n=10) of 6.75±1.75 and an in vitro PFA (n=8) of 6.1.

Example 2
Oil based stick foundation

| | | |
|---|---|---|
| (1) | Carnauba wax | 1.5 wt % |
| (2) | Aristwax | 4.0 |
| (3) | Octylmethoxy cinnamate | 7.5 |
| (4) | Squalane | 30.0 |
| (5) | Liquid paraffin | 12.0 |
| (6) | Kaolin | 5.0 |
| (7) | Kaolin coated with the pongamia extract | 15.0 |
| (8) | Sericite | 7.0 |
| (9) | Red iron oxide | 1.5 |
| (10) | Yellow oxide of iron | 4.0 |
| (11) | Black oxide of iron | 0.5 |
| (12) | Titanium oxide | 7.0 |
| (13) | Nylon powder | 5.0 |
| (14) | Paraben | Appropriate amount |

(Preparation method)

Portion (1)–(5) were heated and dissolved. To this, portion (6)–(14), thoroughly mixed and crushed, were added and mixed while the mixture was stirred. The mixture was then ground and crushed with a colloid mill. After deaeration, the mixture was poured into a container at 70° C. and cooled.

The obtained oil based stick foundation exhibited an in vitro PFA (n=8) of 10.7.

Comparative Example 2
Oil based stick foundation

| | | |
|---|---|---|
| (1) | Carnauba wax | 1.5 wt % |
| (2) | Aristwax | 4.0 |
| (3) | Octylmethoxy cinnamate | 7.5 |
| (4) | Squalane | 30.0 |
| (5) | Liquid paraffin | 12.0 |
| (6) | Kaolin | 20.0 |
| (7) | Kaolin coated with the pongamia extract | — |
| (8) | Sericite | 7.0 |
| (9) | Red iron oxide | 1.5 |
| (10) | Yellow oxide of iron | 4.0 |
| (11) | Black oxide of iron | 0.5 |
| (12) | Titanium oxide | 7.0 |
| (13) | Nylon powder | 5.0 |
| (14) | Paraben | Appropriate amount |

(Preparation method)

Preparation was carried out in the same manner as in Example 2.

The obtained oil based stick foundation exhibited an in vitro PFA (n=8) of 7.8.

Example 3
O/W type emulsified sunscreen cream

| | | |
|---|---|---|
| (1) | Stearic acid | 2.0 wt % |
| (2) | Propylene glycol monostearate | 2.0 |
| (3) | Cetanol | 2.5 |
| (4) | Liquid lanolin | 2.0 |
| (5) | Liquid paraffin | 5.0 |
| (6) | Dimethylpolysiloxane | 5.0 |
| (7) | Purified water | 64.0 |
| (8) | Triethanol amine | 1.0 |
| (9) | Bentonite | 0.8 |
| (10) | Propylene glycol | 5.0 |
| (11) | Paraben | Appropriate amount |
| (12) | Fine particle titanium oxide coated with the pongamia extract | 10.0 |
| (13) | Fine particle titanium oxide | — |

(Preparation method)

The oil phase ingredients (1)–(6) were heated and stirred at 70° C. The water phase was prepared by completely dissolving (7)–(11) and then the powder portion (12) or (13) was mixed into it. The oil phase was then mixed into the water phase and emulsified with a homogenizer. The emulsion was cooled down to 30° C. with a heat exchanger and then put into a container.

The obtained O/W type emulsified sunscreen cream exhibited an in vitro PFA (n=8) of 5.1.

Comparative Example 3
O/W type emulsified sunscreen cream

| | | |
|---|---|---|
| (1) | Stearic acid | 2.0 wt % |
| (2) | Propylene glycol monostearate | 2.0 |
| (3) | Cetanol | 2.5 |
| (4) | Liquid lanolin | 2.0 |
| (5) | Liquid paraffin | 5.0 |
| (6) | Dimethylpolysiloxane | 5.0 |
| (7) | Purified water | 64.0 |
| (8) | Triethanol amine | 1.0 |
| (9) | Bentonite | 0.8 |
| (10) | Propylene glycol | 5.0 |
| (11) | Paraben | Appropriate amount |
| (12) | Fine particle titanium oxide coated with the pongamia extract | — |
| (13) | Fine particle titanium oxide | 10.0 |

(Preparation method)

Preparation was carried out in the same manner as in Example 3.

The obtained O/W type emulsified sunscreen cream exhibited an in vitro PFA (n=8) of 3.5.

Example 4

Emulsified foundation

| | | |
|---|---|---|
| (1) | Dimethylpolysiloxane | 7.0 wt % |
| (2) | Methylphenyl polysiloxane | 5.0 |
| (3) | Decamethylcyclopentasiloxane | 20.0 |
| (4) | Squalane | 2.0 |
| (5) | Trimethylsiloxysilicate | 3.0 |
| (6) | Polyoxyethylene sorbitan fatty acid ester | 3.0 |
| (7) | Polyether modified silicone | 4.0 |
| (8) | Paraben | Appropriate amount |
| (9) | Perfume | Appropriate amount |
| (10) | Fine particle titanium oxide treated with dextrin fatty acid ester | 4.0 |
| (11) | Kaolin treated with dextrin fatty acid ester | 1.0 |
| (12) | Titanium oxide treated with dextrin fatty acid ester | 10.0 |
| (13) | Iron oxide treated with dextrin fatty acid ester | 2.0 |
| (14) | Sericite treated with dextrin fatty acid ester | — |
| (15) | Sericite coated with the pongamia extract | 10.0 |
| (16) | Butylene glyco | 15.0 |
| (17) | Ion exchanged water | 23.9 |

(Preparation method)

The oil phase ingredients (1)–(9) were heated and stirred at 70° C. The powder ingredients (10)–(15) were dispersed and mixed into it. The water phase ingredients (16) and (17) were added to the mixture while emulsification with a homogenizer was conducted. The emulsion was cooled down to 30° C. with a heat exchanger and then put into a container.

The obtained emulsified foundation exhibited an in vitro PFA (n=8) of 11.8.

Comparative Example 4

Emulsified foundation

| | | |
|---|---|---|
| (1) | Dimethylpolysiloxane | 7.0 wt % |
| (2) | Methylphenyl polysiloxane | 5.0 |
| (3) | Decamethylcyclopentasiloxane | 20.0 |
| (4) | Squalane | 2.0 |
| (5) | Trimethylsiloxysilicicate | 3.0 |
| (6) | Polyoxyethylene sorbitan fatty acid ester | 3.0 |
| (7) | Polyether modified silicone | 4.0 |
| (8) | Paraben | Appropriate amount |
| (9) | Perfume | Appropriate amount |
| (10) | Fine particle titanium oxide treated with dextrin fatty acid ester | 4.0 |
| (11) | Kaolin treated with dextrin fatty acid ester | 1.0 |
| (12) | Titanium oxide treated with dextrin fatty acid ester | 10.0 |
| (13) | Iron oxide treated with dextrin fatty acid ester | 2.0 |
| (14) | Sericite treated with dextrin fatty acid ester | 10.0 |
| (15) | Sericite coated with the pongamia extract | — |
| (16) | Butylene glycol | 5.0 |
| (17) | Ion exchanged water | 23.9 |

(Preparation method)

Preparation was carried out in the same manner as in Example 4.

The obtained emulsified foundation exhibited an in vitro PFA (n=8) of 8.6.

Example 5

W/O type emulsified solid foundation

| | | |
|---|---|---|
| (1) | Dimethylpolysiloxane | 10.0 wt % |
| (2) | Methylphenyl polysiloxane | 5.0 |
| (3) | Decamethylcyclopentasiloxane | 15.0 |
| (4) | Squalane | 2.0 |
| (5) | Glyceryl tri (2-ethylhexanoate) | 3.0 |
| (6) | Solid paraffin | 8.0 |
| (7) | Carnauba wax | 3.0 |
| (8) | Polyoxyethylene sorbitan fatty acid ester | 1.0 |
| (9) | Polyether modified silicone | 1.0 |
| (10) | Fine particle titanium oxide treated with silicone resin | 6.0 |
| (11) | Titanium oxide treated with silicone resin | 2.0 |
| (12) | Iron oxide treated with silicone resin | 2.0 |
| (13) | Sericite treated with silicone resin | 18.0 |
| (14) | Spherical acrylic resin powder coated with the pongamia extract | 12.0 |
| (15) | Butylene glycol | 5.0 |
| (16) | Paraben | Appropriate amount |
| (17) | Ion exchanged water | Balance |

(Preparation method)

The oil phase ingredients (1)–(9) were heated and stirred at 90° C. The powder ingredients (10)–(14) were dispersed and mixed into it. The water phase ingredients (15)–(17) were added to the mixture while emulsification with a homogenizer was conducted. The emulsion was put into a container.

The obtained W/O type emulsified solid foundation exhibited an in vitro PFA (n=8) of 6.3.

Comparative Example 5

W/O type emulsified solid foundation

| | | |
|---|---|---|
| (1) | Dimethylpolysiloxane | 10.0 wt % |
| (2) | Methylphenyl polysiloxane | 5.0 |
| (3) | Decamethylcyclopentasiloxane | 15.0 |
| (4) | Squalane | 2.0 |
| (5) | Glyceryl tri (2-ethylhexanoate) | 3.0 |
| (6) | Solid paraffin | 8.0 |
| (7) | Carnauba wax | 3.0 |
| (8) | Polyoxyethylene sorbitan fatty acid ester | 1.0 |
| (9) | Polyether modified silicone | 1.0 |
| (10) | Fine particle titanium oxide treated with silicone resin | 6.0 |
| (11) | Titanium oxide treated with silicone resin | 2.0 |
| (12) | Iron oxide treated with silicone resin | 2.0 |
| (13) | Sericite treated with silicone resin | 18.0 |
| (14) | Spherical acrylic resin powder | 12.0 |
| (15) | Butylene glycol | 5.0 |
| (16) | Paraben | Appropriate amount |
| (17) | Ion exchanged water | Balance |

(Preparation method)

The oil phase ingredients (1)–(9) were heated and stirred at 90° C. The powder ingredients (10)–(14) were dispersed and mixed into it. The water phase ingredients (15)–(17) were added to the mixture while emulsification with a homogenizer was conducted. The emulsion was put into a container.

The obtained W/O type emulsified solid foundation exhibited an in vitro PFA (n=8) of 3.9.

Example 6
White powder

| | | |
|---|---|---|
| (1) | Talc coated with the pongamia extract (6%) | 90.82 wt % |
| (2) | Zinc white | 1.0 |
| (3) | Aluminum-stearate-processed titanium dioxide | 1.0 |
| (4) | Iron oxide | 0.2 |
| (5) | Paraben | Appropriate amount |
| (6) | Squalane | 2.0 |
| (7) | Vaseline | 2.5 |
| (8) | Sorbitan sesqui isostearate | 0.3 |
| (9) | Antioxidant | Appropriate amount |
| (10) | Perfume | Appropriate amount |

The obtained white powder exhibited an in vitro SPF value of 7.1 and an in vitro PFA (n=8) of 2.9.

Example 7
White powder

| | | |
|---|---|---|
| (1) | Talc coated with the pongamia extract (6%) | 90.82 wt % |
| (2) | Zinc white | 1.0 |
| (3) | Aluminum-stearate-processed titanium dioxide | 1.0 |
| (4) | Iron oxide | 0.2 |
| (5) | Paraben | Appropriate amount |
| (6) | Octylmethoxy cinnamate | 2.0 |
| (7) | Vaseline | 2.5 |
| (8) | Sorbitan sesqui isostearate | 0.3 |
| (9) | Antioxidant | Appropriate amount |
| (10) | Perfume | Appropriate amount |

The obtained white powder exhibited an in vitro SPF value of 21.8 and an in vitro PFA (n=8) of 8.2.

Comparative Example 6
White powder

| | | |
|---|---|---|
| (1) | Talc coated with metal soap | 90.82 wt % |
| (2) | Zinc white | 1.0 |
| (3) | Aluminum-stearate-processed titanium dioxide | 1.0 |
| (4) | Iron oxide | 0.2 |
| (5) | Paraben | Appropriate amount |
| (6) | Squalane | 2.0 |
| (7) | Vaseline | 2.5 |
| (8) | Sorbitan sesqui isostearate | 0.3 |
| (9) | Antioxidant | Appropriate amount |
| (10) | Perfume | Appropriate amount |

The obtained white powder exhibited an in vitro SPF value of 13.2 and an in vitro PFA (n=8) of 7.5.

Example 8
W/O type emulsified sunscreen agent

| | | |
|---|---|---|
| (1) | Liquid paraffin | 5.0 wt % |
| (2) | Octylmethoxy cinnamate | 7.5 |
| (3) | Decamethyl pentasiloxane | 17.95 |
| (4) | Polyether modified silicone | 2.0 |
| (5) | Aluminum-stearate-processed titanium dioxide | 1.0 |
| (6) | Talc coated with the pongamia extract (6%) | 18.0 |
| (7) | Butylene glycol | 6.0 |
| (8) | Paraben | Appropriate amount |
| (9) | Smectite | 0.7 |
| (10) | Dispersing agent | 1.0 |
| (11) | Ion exchanged water | Balance |

The obtained white powder exhibited an in vitro PFA (n=8) of 1.2.

Comparative Example 7
W/O type emulsified sunscreen agent

| | | |
|---|---|---|
| (1) | Liquid paraffin | 5.0 wt % |
| (2) | Octylmethoxy cinnamate | 7.5 |
| (3) | Decamethyl pentasiloxane | 17.95 |
| (4) | Polyether modified silicone | 2.0 |
| (5) | Aluminum-stearate-processed titanium dioxide | 1.0 |
| (6) | Talc coated with metal soap | 18.0 |
| (7) | Butylene glycol | 6.0 |
| (8) | Paraben | Appropriate amount |
| (9) | Smectite | 0.7 |
| (10) | Dispersing agent | 1.0 |
| (11) | Ion exchanged water | Balance |

The obtained white powder exhibited an in vitro PFA (n=8) of 4.3.

Figure 4:
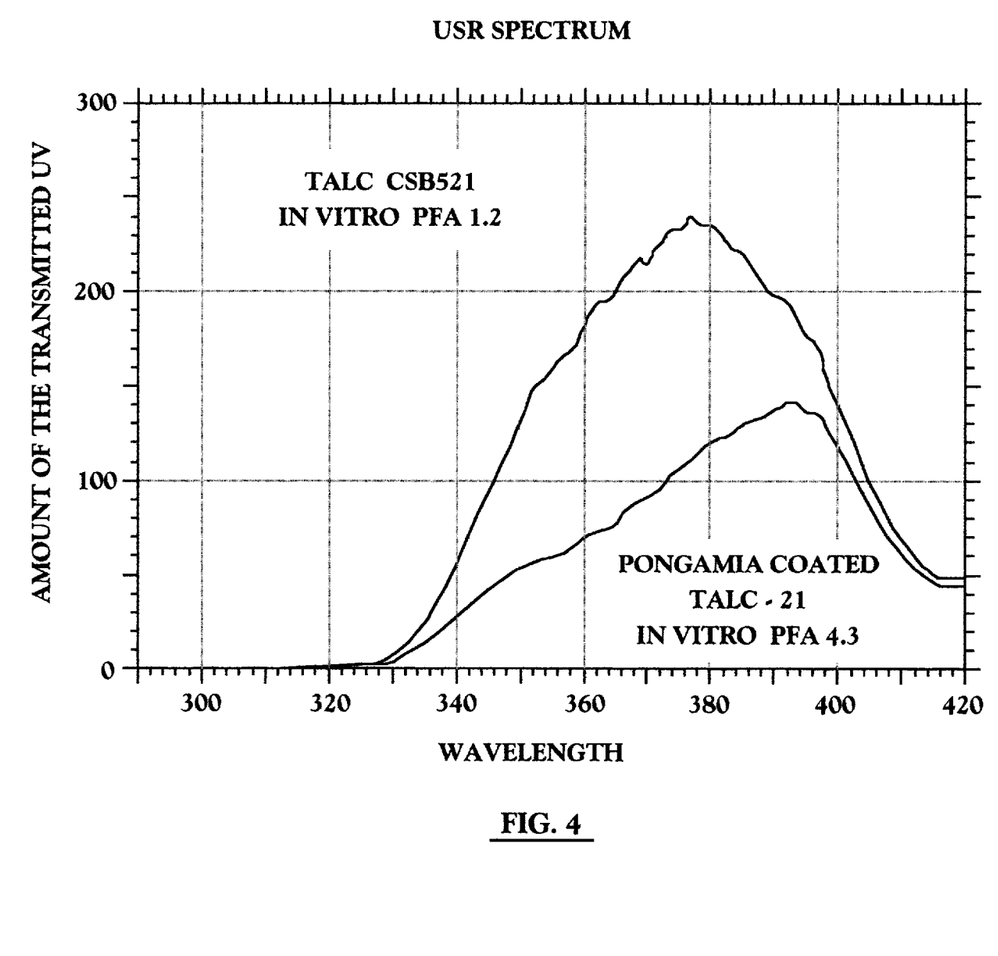
FIG. 4 shows the transmitted UV light spectra for cases where W/O emulsion type sunscreen agents of Example 8 and Comparative example 7 were irradiated with light of a prescribed intensity.

The W/O emulsified sunscreen agents of Example 8 and Comparative example 7 were applied on tapes (product name: "Transpore" from 3M Co., Ltd.) and they were irradiated with a 150 W Xe arc lamp with a constant intensity. The transmitted UV light was detected with a spectroradio meter. The in vivo FPA was calculated based on the spectra. The spectra are shown in FIG. 4.

INDUSTRIAL APPLICABILITY OF THE INVENTION

As described thus far, the powder treated with the sparingly soluble ultraviolet light absorber of the present invention allows the sparingly soluble ultraviolet light absorber to be blended in a high concentration in the system and to be blended homogeneously in the base agent, and moreover, the cosmetic which contains the powder treated with the sparingly soluble ultraviolet light absorber of the present invention exhibits superior stability over time.

What is claimed is:

1. Powder coated with a sparingly soluble ultraviolet light absorber which is prepared by coating the surface of inorganic powder or organic powder with the sparingly soluble ultraviolet light absorber, said soluble ultraviolet light absorber comprises 4-(3,4-dimethoxyphenylmethylene)-2,5-dioxoimidazolidine-1-propionic acid 2-ethylhexyl ester, dibenzoyl methane derivatives and Chalcone derivatives.

2. Powder coated with the sparingly soluble ultraviolet light absorber of claim 1 wherein the ultraviolet light absorber refers to a ultraviolet light absorber whose solubility in isopropyl myristate at room temperature is 2% or less.

3. Powder coated with the sparingly soluble ultraviolet light absorber wherein the sparingly soluble ultraviolet light absorber is a pongamia extract.

4. A powder-containing cosmetic which contains the powder coated with the sparingly soluble ultraviolet light absorber of claim 1.

5. A powder-containing cosmetic which contains the powder coated with the sparingly soluble ultraviolet light absorber of claim 2.

6. A powder-containing cosmetic which contains the powder coated with the sparingly soluble ultraviolet light absorber of claim 3.

* * * * *